United States Patent
Kabalnova et al.

(10) Patent No.: US 12,286,531 B2
(45) Date of Patent: Apr. 29, 2025

(54) MULTI-BLOCK COPOLYMER COMPOSITIONS

(71) Applicant: REVA Medical, Inc., San Diego, CA (US)

(72) Inventors: Lioubov Kabalnova, San Diego, CA (US); Durgadas Bolikal, San Diego, CA (US); Ernest G. Baluca, San Diego, CA (US); Jessica Earley, Carlsbad, CA (US)

(73) Assignee: REVA Medical, Inc., San Diego, CA (US)

( * ) Notice: Subject to any disclaimer, the term of this patent is extended or adjusted under 35 U.S.C. 154(b) by 1082 days.

(21) Appl. No.: 16/969,124

(22) PCT Filed: Feb. 4, 2019

(86) PCT No.: PCT/US2019/016465
§ 371 (c)(1),
(2) Date: Aug. 11, 2020

(87) PCT Pub. No.: WO2020/032999
PCT Pub. Date: Feb. 13, 2020

(65) Prior Publication Data
US 2021/0040314 A1  Feb. 11, 2021

Related U.S. Application Data

(60) Provisional application No. 62/715,978, filed on Aug. 8, 2018.

(51) Int. Cl.
| | | |
|---|---|---|
| *A61L 31/14* | (2006.01) | |
| *A61L 31/06* | (2006.01) | |
| *A61L 31/16* | (2006.01) | |
| *A61L 31/18* | (2006.01) | |
| *C08G 63/64* | (2006.01) | |
| *C08L 69/00* | (2006.01) | |

(52) U.S. Cl.
CPC ............. *C08L 69/005* (2013.01); *A61L 31/06* (2013.01); *A61L 31/16* (2013.01); *A61L 31/18* (2013.01); *C08G 63/64* (2013.01); *C08L 2203/02* (2013.01); *C08L 2205/025* (2013.01); *C08L 2207/02* (2013.01)

(58) Field of Classification Search
CPC .............. C08L 69/005; C08L 2203/02; C08L 2205/025; C08L 2207/02; A61L 31/06; A61L 31/16; A61L 31/18; C08G 63/64
See application file for complete search history.

(56) References Cited

U.S. PATENT DOCUMENTS

| | | |
|---|---|---|
| 7,939,611 B2 | 5/2011 | Brandom et al. |
| 8,252,887 B2 | 8/2012 | Durgadas et al. |
| 8,476,399 B2 | 7/2013 | Bolikal et al. |
| 8,551,511 B2 | 10/2013 | Brandom et al. |
| 9,416,090 B2 | 8/2016 | Kohn et al. |
| 2006/0034769 A1 | 2/2006 | Kohn et al. |
| 2010/0030313 A1 | 2/2010 | Edelman |
| 2011/0212050 A1 | 9/2011 | Brandom et al. |
| 2013/0203713 A1* | 8/2013 | Kohn |
| 2015/0045451 A1 | 2/2015 | Bolikal et al. |
| 2017/0009021 A1 | 1/2017 | Meyer et al. |

FOREIGN PATENT DOCUMENTS

| | | |
|---|---|---|
| WO | WO 2013/116804 | 8/2013 |
| WO | WO 2017/111994 | 6/2017 |

OTHER PUBLICATIONS

Matsushita (Encyclopedia of Polymeric Nanomaterials, pp. 1-6, published 2014) (Year: 2014).*
Extended European Search Report issued in EP Application No. 19846878.7 dated Aug. 4, 2022.
Partial Supplementary European Search Report issued in corresponding EP Application No. 19846878.7, dated Apr. 12, 2022.
Written Opinion and Search Report issued in International Application No. PCT/US2019/016465 dated Apr. 10, 2019.
Office Action issued in JP Application No. 2020543205 dated Jan. 5, 2023.
Office Action issued in JP Application No. 2020543205 dated Oct. 3, 2023.
Office Action issued in AU Application No. 2019317250 dated May 14, 2024.
Office Action issued in CA Application No. 3,091,121 dated Jan. 31, 2024.
Office Action issued in JP Application No. 2020543205 dated Jul. 8, 2024.

* cited by examiner

*Primary Examiner* — Alma Pipic
(74) *Attorney, Agent, or Firm* — Knobbe, Martens, Olson & Bear, LLP

(57) ABSTRACT

Methods of making multi-block copolymer that reduce the tendency for large phase domains to form provide copolymer compositions that are useful for various applications, including the manufacture of medical devices.

26 Claims, 7 Drawing Sheets

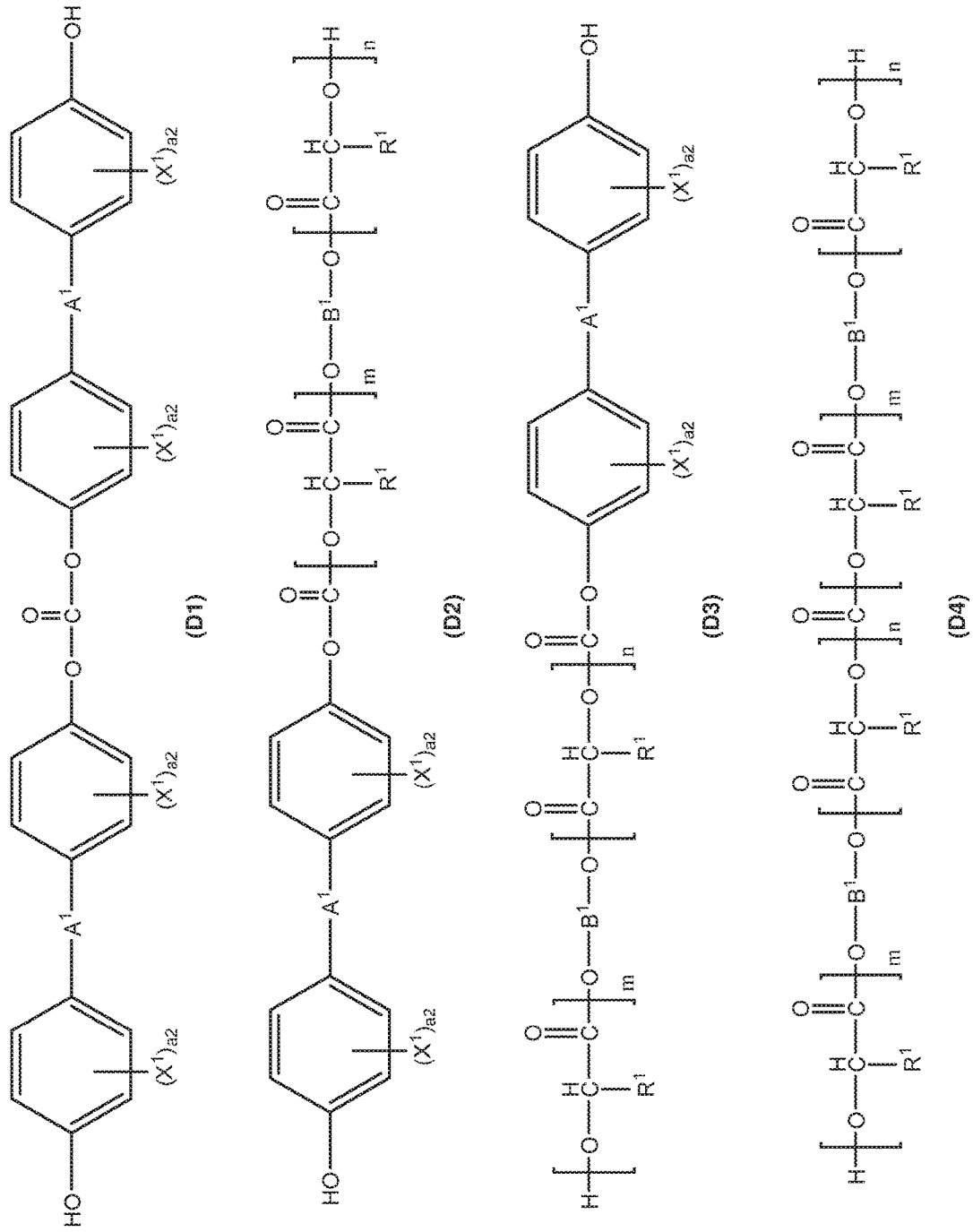

Table 1. Absolute density of blown tubes formed from block-copolymer Poly(50% PrD-di I2DAT-co-50% EGPI/LAD7k) carbonate with different degrees of phase separation

| Average size of discontinuous domain | Density, g/cm³ | SEM image |
|---|---|---|
| Single phase | 1.6242 ± 0.0021 |  |
| 1 μm ≤ Size ≤ 5 μm | 1.6094 ± 0.0017 |  |
| 5 μm ≤ Size ≤ 10 μm | 1.5751 ± 0.0016 |  |

MULTI-BLOCK COPOLYMER COMPOSITIONS

RELATED APPLICATION

This application claims priority to U.S. Provisional Application No. 62/715,978, filed Aug. 8, 2018, the entirety of which is hereby incorporated herein by reference.

BACKGROUND

Field

This application relates to multi-block copolymers and methods of making them that reduce or eliminate the tendency for copolymer compositions to contain large phase domains, and to medical devices that include such materials.

Description of the Related Art

A number of copolymers have been developed for medical applications, including those described in U.S. Pat. Nos. 8,252,887; 8,476,399; 8,551,511; and 9,416,090, as well as those described in U.S. Patent Application Publication No. 2015/0045451. Some of the copolymer compositions described in these patent publications exhibit a degree of phase separation that enhances mechanical properties such as fracture and/or fatigue toughness. See, for example, U.S. Pat. No. 8,551,511. The disclosures of U.S. Pat. Nos. 8,252,887; 8,476,399; 8,551,511; and 9,416,090, as well as the disclosure of U.S. Patent Application Publication No. 2015/0045451, are hereby incorporated herein by reference, and particularly for the purpose of describing the copolymer compositions and the methods of making them described therein.

SUMMARY

It has now been discovered that certain aspects of multi-block copolymer phase separation can have a detrimental effect on the properties of copolymer compositions, and particularly in compositions that contain multi-block copolymers having a strong tendency to form large discontinuous domains of a first polymer phase that are dispersed in a continuous second polymer phase. For example, it has now been found that certain copolymer compositions exemplified by those described in Example 21 of U.S. Pat. No. 9,416,090 have a morphology characterized by undesirably large discontinuous phase domains as illustrated in FIG. 1. Previously, it was believed that such morphologies were a consequence of the relative amounts of the diol comonomers that were copolymerized together with triphosgene (a source of phosgene) to make the multi-block copolymers. Thus, even if copolymerization of a selected combination of comonomers resulted in a desirable balance of properties for the resulting multi-block copolymer per se, it was believed that the morphology (e.g., phase structure) of the copolymer composition at thermodynamic equilibrium was dictated by its chemical composition and thus difficult to meaningfully alter.

Surprisingly, it has now been found that the morphology of a copolymer composition can be enhanced by controlling the makeup of its multi-block copolymer constituents. For example, a multi-block copolymer made from the same combination of comonomers as Example 21 of U.S. Pat. No. 9,416,090 can be made in accordance with the teachings provided herein to have the form of a copolymer composition having desirably smaller discontinuous domains as illustrated in FIG. 2 or a copolymer composition having essentially no phase separation as illustrated in FIG. 3.

Accordingly, various embodiments provide copolymer compositions, methods of making them and medical devices that include such copolymer compositions, as described in greater detail below.

An embodiment provides a copolymer composition, comprising:
a multi-block copolymer comprising a first block and a second block, wherein the first block is substituted with an amount of heavy atoms that is effective to render it more radiopaque than the second block and wherein the multi-block copolymer has a number average molecular weight of 100 kDa or greater;
wherein the multi-block copolymer is in the form of a single phase having a glass transition temperature for the single phase that is greater than 37° C.; or
wherein the copolymer composition comprises a discontinuous first polymer phase having a first glass transition temperature greater than 37° C. and a continuous second polymer phase having a second glass transition temperature greater than 37° C., the discontinuous first polymer phase being relatively enriched in the first blocks of the multi-block copolymer and the continuous second polymer phase being relatively enriched in the second blocks of the multi-block copolymer.

Another embodiment provides a method of making a copolymer composition as described herein, comprising copolymerizing an aromatic diol monomer of the Formula (A1a) and an aliphatic diol monomer of the Formula (B1a) in the presence of a phosgene source under reaction conditions selected to form the multi-block copolymer.

Another embodiment provides an implantable medical device (such as a stent) that comprises a copolymer composition as described herein.

These and other embodiments are described in greater detail below.

BRIEF DESCRIPTION OF THE DRAWINGS

FIGS. 4A, 4B and 4C illustrates aspects of the copolymerization reaction kinetics between phosgene (COCl$_2$) and comonomers of the Formulae (A1a) and (B1a).

DETAILED DESCRIPTION

Definitions

Figure 1:
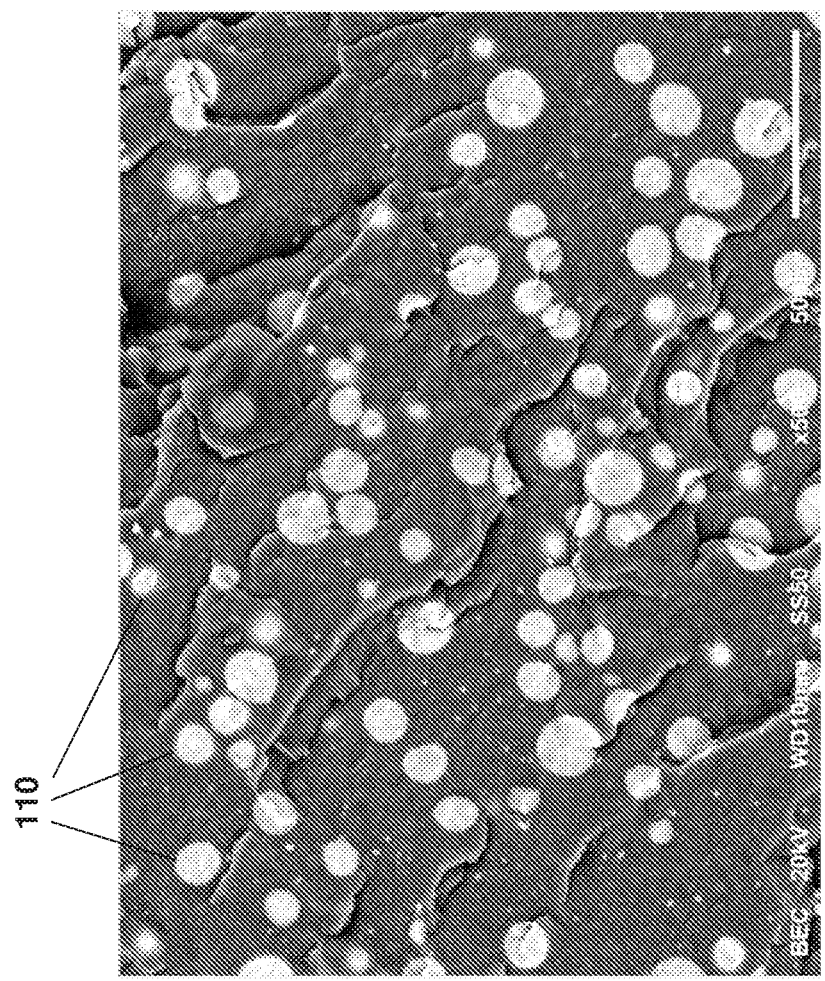
FIG. 1 depicts a scanning electron microscopy (SEM) photomicrograph of the multi-block copolymer of Comparative Example 1, illustrating phase separation between large discontinuous domains 110 of the first polymer phase (relatively enriched in blocks of PrD-di I$_2$DAT) that are dispersed in the continuous second polymer phase (relatively enriched in the blocks of EGPLLAD7k).

The term "glass transition temperature" as used herein has its usual meaning as understood by those skilled in the art and thus refers to the temperature at which a polymeric material or phase undergoes a second order thermal transition from the glassy state to the rubbery state, as determined by differential scanning calorimetry (DSC).

The term "heavy atom" as used herein has its usual meaning as understood by those skilled in the art in the context of describing atoms that confer radiopacity to a polymer, and thus includes bromine and iodine.

The term "medical device" as used herein has its usual meaning as understood by those skilled in the art, and thus includes products that meet the U.S. Food and Drug Administration definition of a medical device as set forth in section 201(h) of the Federal Food, Drug and Cosmetic Act.

The term "multi-block copolymer" as used herein has its usual meaning as understood by those skilled in the art and thus includes copolymers that contain two or more different homopolymeric subunits linked by covalent bonds.

The terms "organic spacer", "organic spacer group", "linking group" and similar terms as used herein in the context of describing chemical structures have their usual meaning as understood by those skilled in the art and thus include generally linear groups that contain any number of carbon atoms in the range from one to thirty and that are bonded to the remainder of the chemical structure in two or more places, typically at the ends. In various embodiments the number of carbon atoms in the organic spacer group can be any integer in the range of 1 to 2, 1 to 4, 1 to 6, 1 to 8, 1 to 10, 1 to 12, 1 to 15, 1 to 20, 2 to 4, 2 to 6, 2 to 8, 2 to 10, 2 to 12, 2 to 15, 2 to 20, 2 to 30, 4 to 6, 4 to 8, 4 to 10, 4 to 12, 4 to 15, 4 to 20, 4 to 30 or 7 to 18. Non-limiting examples of organic spacer groups include $C_{1-30}$ alkylene (e.g., $-(CH_2)_{1-30}-$), $C_{2-30}$ oxyalkylene (e.g., $-(CH_2CH_2O)_{1-15}-$), $C_{1-30}$ diol (e.g., $-O-(CH_2)_{1-30}-O-$), $C_{4-30}$ dicarboxyalkylene (e.g., $-O-(C=O)-(CH_2)_{2-28}-(C=O)-O-$ and $-(C=O)-O-(CH_2)_{2-28}-O-(C=O)-$), $C_{8-30}$ diesteralkylene (e.g., $-CH_2CH_2-O-(C=O)-(CH_2)_{2-24}-(C=O)-O-CH_2CH_2-$ and $-CH_2CH_2-(C=O)-O-(CH_2)_{2-24}-O-(C=O)-CH_2CH_2-$), $C_{4-30}$ diamidoalkylene (e.g., $-NH-(C=O)-(CH_2)_{2-28}-(C=O)-NH-$ and $-(C=O)-NH-(CH_2)_{2-28}-NH-(C=O)-$), $C_{4-30}$ dicarbonatoalkylene (e.g., $-O-(C=O)-O-(CH_2)_{2-28}-O-(C=O)-O-$) and $C_{2-30}$ oxyalkylene diol (e.g., $-O-(CH_2O)_{2-30}-$). Those skilled in the art will recognize that the foregoing examples of organic spacer groups have been illustrated as having a number of carbon atoms in a particular range (e.g., $C_{1-30}$), but that the number of carbon atoms is not so limited, and thus such examples of organic spacer groups may include the numbers of carbon atoms in the various ranges described in this paragraph or elsewhere herein. For example, in an embodiment, the organic spacer group is a diesteralkylene of the formula $-CH_2CH_2-(C=O)-O-(CH_2)_{a1}-O-(C=O)-CH_2CH_2-$, where a1 is in the range of 1 to 12.

The terms "phase separated", "phase separation" and similar terms as used herein have their usual meanings as understood by those skilled in the art and thus include reference to polymer compositions that contain two or more polymeric regions that are immiscible in one another to a degree that allows the separate regions to be detected by scanning electron microscopy (SEM) and/or DSC. For example, a phase separated multi-block copolymer contains separate regions, each relatively enriched in one or another of the different homopolymeric subunits contained in the copolymer. In some cases imaging of the separate phases by SEM can be aided by elemental microanalysis techniques known to those skilled in the art, such as energy dispersive X-ray spectrometry (EDS). In many cases SEM and DSC are particularly effective when used together to detect the phases in a phase separated multi-block copolymer.

Copolymer Compositions

It has now been found that certain copolymer compositions have a morphology characterized by large discontinuous phase domains 110 as illustrated in FIG. 1. For example, scanning electron microscopy (SEM) shows that the copolymer composition of Comparative Example 1 below, which was prepared as described in Example 21 of U.S. Pat. No. 9,416,090, contains a first polymer phase (relatively enriched in PrD-di I$_2$DAT units) in the form of large discontinuous domains 110 that are dispersed in a continuous second polymer phase (relatively enriched in EGPLLAD7k units). Surprisingly, the average size of the large discontinuous phase domains 110 is about 15 μm, indicating that the multi-block copolymer formed by the process of Example 21 of U.S. Pat. No. 9,416,090 was highly blocky, containing relatively long sequences enriched in blocks of PrD-di I$_2$DAT as well as relatively long sequences enriched in blocks of EGPLLAD7k.

As indicated in Comparative Example 1 below, the multi-block copolymer formed by the process of Example 21 of U.S. Pat. No. 9,416,090 had a number average molecular weight of about 75 kDa. Thus, the morphology illustrated in FIG. 1 is not driven by the phase separation of low molecular weight oligomers. Those skilled in the art understand the relationship between the time of polymerization and the degree of polymerization in the context of the kinetics of step polymerization. In particular, the average molecular weight increases relatively slowly during a step polymerization, as monomers react with one another to form dimers, dimers react with monomers to form trimers, dimers react with dimers to form tetramers, etc. Thus, significant quantities of high molecular weight polymers are not generally formed in step polymerizations until the final stages of the reaction, by which time low molecular weight oligomers are at extremely low levels. It is also important to note that the multi-block copolymer of Example 21 of U.S. Pat. No. 9,416,090 was prepared without rigorous drying of initial monomers and under uncontrolled temperature conditions.

Those skilled in the art also understand that high molecular weight polymers are not formed from reactions between bifunctional monomers (e.g., reactions between A-A and B-B comonomers, where functional group A reacts only with functional group B) unless the reaction stoichiometry is precisely controlled to be as close to a 1:1 molar ratio of the reacting functional groups as practical. Thus, for example, in the reaction between a diol (e.g., HO—R—OH) and phosgene (Cl—CO—Cl) to form a polycarbonate, high molecular weight is achieved by careful stoichiometric control. Even a small excess of diol will result in a relatively low molecular weight mixture of various hydroxy end-capped oligomers, and a small excess of phosgene will result in a similar oligomeric mixture but end-capped with chloroformate groups. In such a polymerization, diols cannot be connected to one another without phosgene, and vice versa, so blocks of one or the other cannot easily be formed by manipulating reaction conditions, such as by employing an excess of either monomer.

The step polymerization reaction described in Example 21 of U.S. Pat. No. 9,416,090 illustrates the copolymerization of monomers that contain multiple functional groups of differing reactivity, in particular triphosgene (a phosgene source) and two diols (PrD-di I$_2$DAT and EGPLLAD). Those skilled in the art understand that the step polymerization kinetics for reactions between monomers that contain multiple functional groups of differing reactivity are much more complicated than when only pairs of bifunctional monomers are involved. Thus, except for very well-understood step polymerizations (typically those of significant commercial or academic focus), there is generally little or no expectation that the sequence distribution or blockiness of a copolymer can be controlled by manipulating reaction conditions for a step polymerization of three or more different comonomers having functional groups of differing reactivity. Thus, the surprising degree of blockiness discovered for the multi-block copolymer formed by the process of Example 21 of U.S. Pat. No. 9,416,090 was unexpected.

Figure 2:
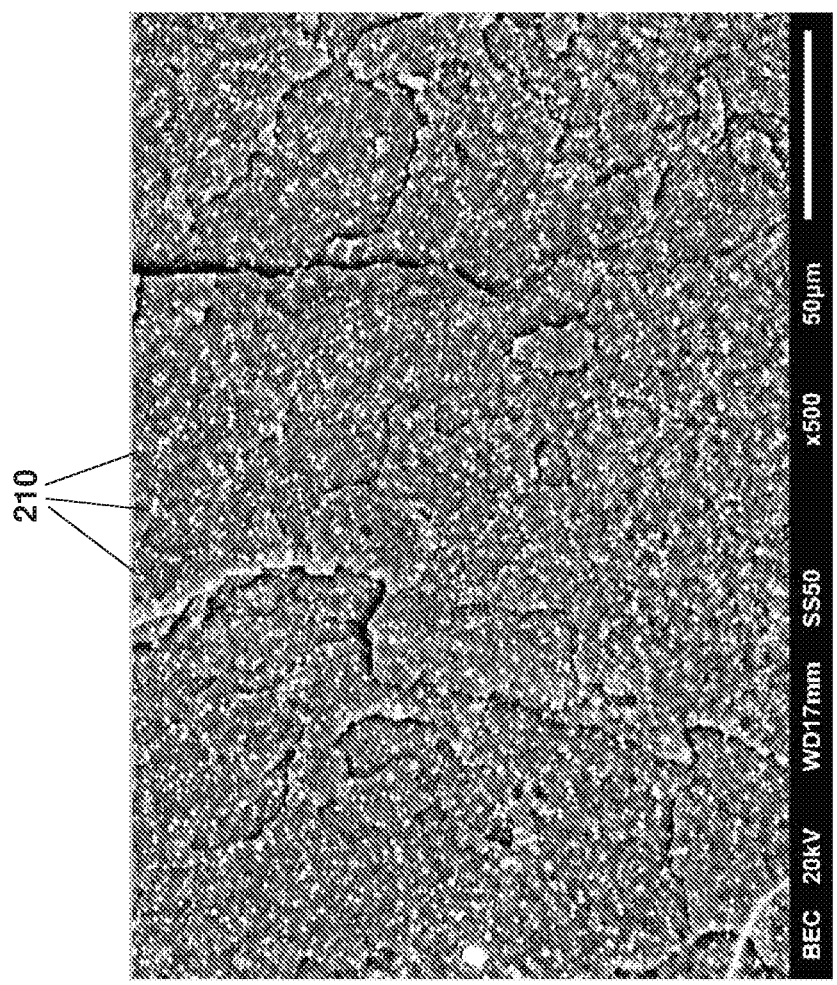
FIG. 2 depicts an SEM photomicrograph of the multi-block copolymer of Example 2, illustrating phase separation between smaller (as compared to FIG. 1) discontinuous domains 210 of the first polymer phase (relatively enriched in blocks of PrD-di I$_2$DAT) that are dispersed in the continuous second polymer phase (relatively enriched in the blocks of EGPLLAD7k).
Figure 3:
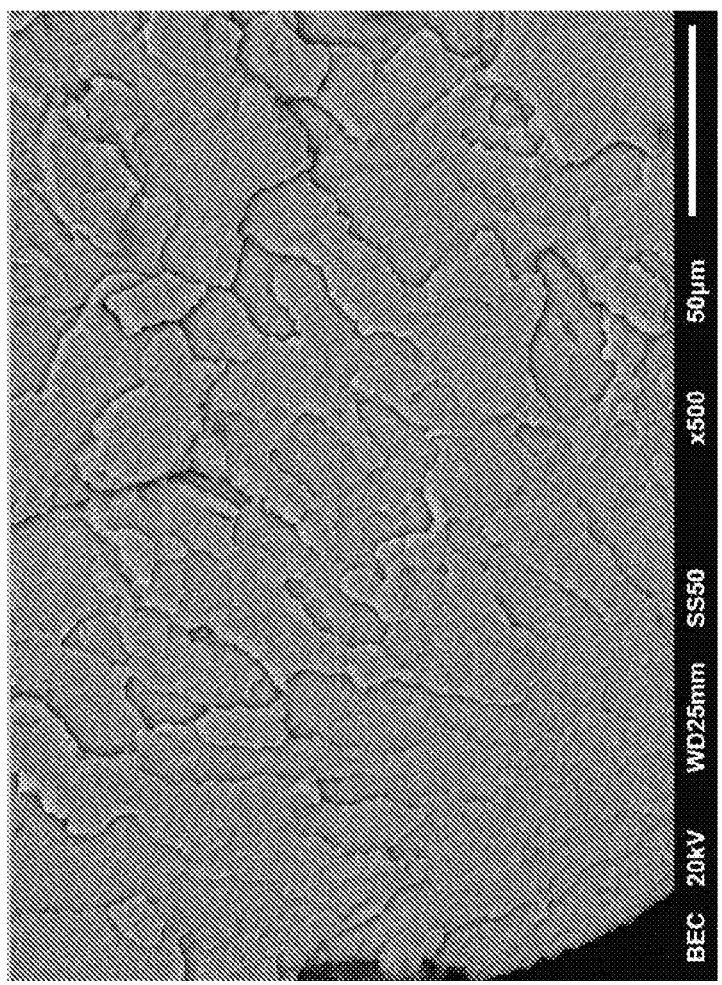
FIG. 3 depicts an SEM photomicrograph of the multi-block copolymer of Example 3, illustrating the lack of phase separation (at this magnification by SEM) between the blocks of PrD-di I$_2$DAT and the blocks of EGPLLAD7k.

Copolymer compositions have now been developed that exhibit smaller domain sizes that are indicative of a lower degree of blockiness. For example, FIG. 2 depicts an SEM photomicrograph of the multi-block copolymer of Example 2, illustrating phase separation in the form of smaller discontinuous domains 210 as compared to FIG. 1, and FIG. 3 depicts an SEM photomicrograph of the multi-block copolymer of Example 3, illustrating a lack of visible phase separation at this SEM magnification as compared to FIG. 1 and FIG. 2. As described below, the multi-block copolymers of Example 2 and Example 3 were prepared using the same amounts of the same monomers used to prepare the multi-block copolymer of Comparative Example 1. Thus, the copolymer composition of Example 2 also contains a first polymer phase (relatively enriched in PrD-di I$_2$DAT units) in the form of discontinuous domains 210 that are dispersed in a continuous second polymer phase (relatively enriched in EGPLLAD7k units), but the domains 210 have an average domain size that is less than 10 µm, indicating that the multi-block copolymer of Example 2 is less blocky than that of Comparative Example 1. The copolymer of Example 3 does not exhibit any visible phase separation by the SEM method used (FIG. 3), indicating that the multi-block copolymer is in the form of a single phase and that it is even less blocky than the multi-block copolymer of Example 2. This unexpected decrease in average domain size (FIG. 2) and the unexpected formation of a single phase multi-block copolymer (FIG. 3) was achieved by judicious selection of polymerization conditions that favor a more random (and thus less blocky) incorporation of PrD-di I$_2$DAT and EGPLLAD7k units into the polymer.

Figure 4A:
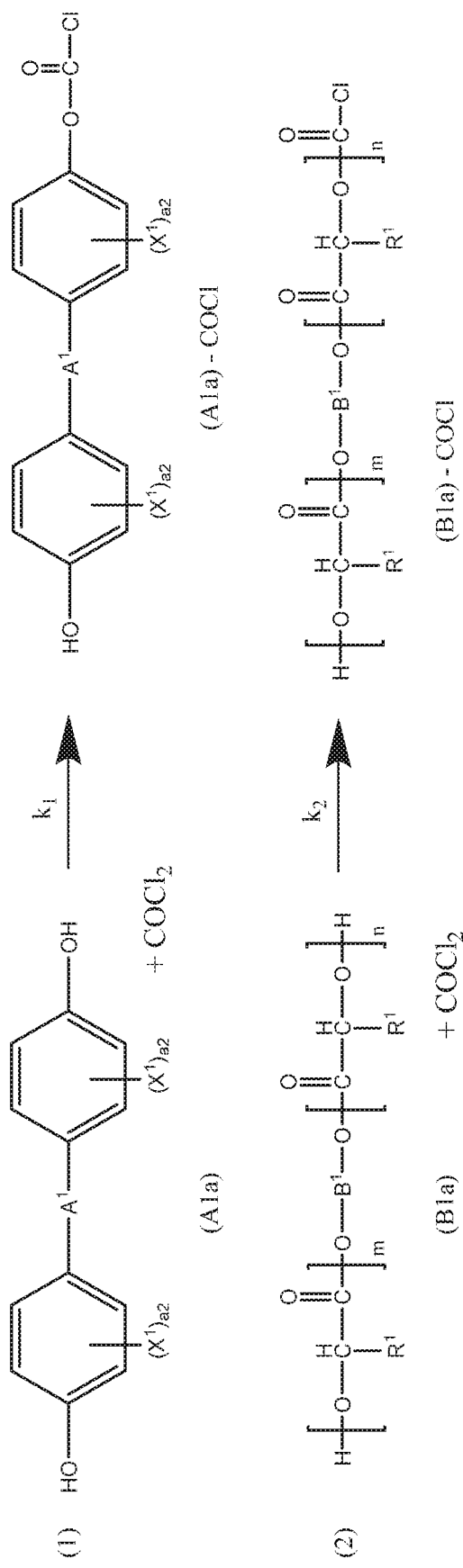
Figure 4B:
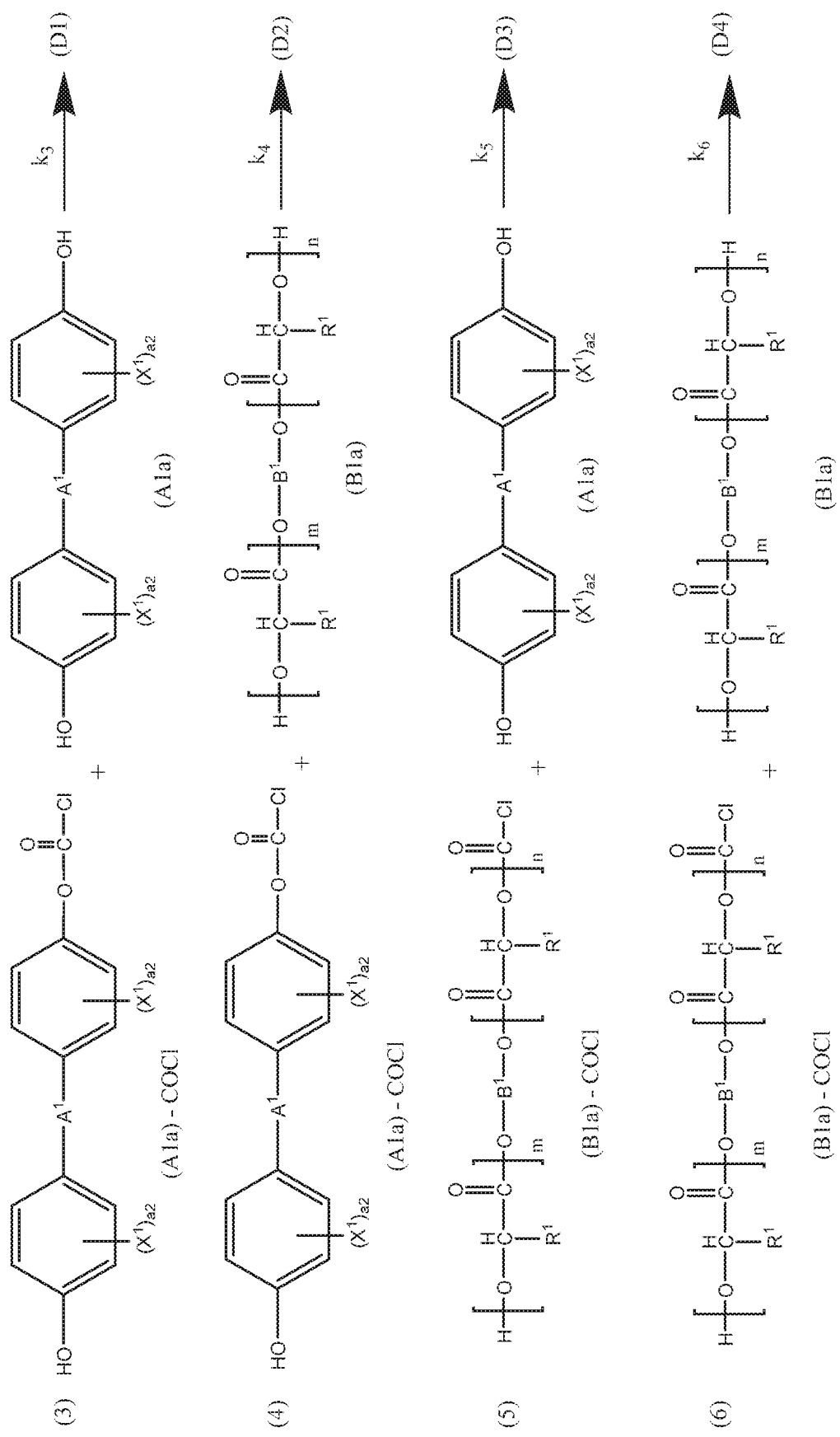

This invention is not limited by theory of operation, but it is believed that such polymerization conditions enhance the relative rate at which the less reactive comonomer is incorporated into the polymer. A simplified series of reaction schemes that illustrates the complex kinetics of such multicomponent polymerization systems is depicted in FIGS. 4A to 4C. In the illustrated system, phosgene is reacted with a mixture of an aromatic diol monomer represented by the Formula (A1a) and an aliphatic diol monomer of the Formula (B1a), for which the variables $A^1$, $B^1$, $R^1$, $X^1$, a2, m and n are described elsewhere herein. Those skilled in the art will recognize that PrD-di I$_2$DAT is a specific example of a monomer of Formula (A1a) and that EGPLLAD7k (having a number average molecular weight of about 7 kDa) is a specific example of a monomer of Formula (B1a). Thus, FIGS. 4A to 4C provide a simplified illustration of the reaction kinetics for the copolymerization conditions of Comparative Example 1 and Examples 2-3.

In FIG. 4A, reaction scheme (1) illustrates the reaction of monomer (A1a) with phosgene at rate constant $k_1$ to form the chloroformate monomer (A1a)-COCl. Similarly, reaction scheme (2) illustrates the reaction of monomer (B1a) with phosgene at rate constant $k_2$ to form the chloroformate monomer (B1a)-COCl. As illustrated in FIG. 4B, each of the two chloroformate monomers (A1a)-COCl and (B1a)-COCl can react with an additional monomer of either Formula (A1a) or Formula (B1a), as indicated by the four reaction schemes (3), (4), (5) and (6) and the respective rate constants $k_3$, $k_4$, $k_5$ and $k_6$, to form carbonate dimers (D1), (D2), (D3), and (D4), respectively, having the chemical structures illustrated in FIG. 4C. Those skilled in the art will appreciate that the carbonate dimers (D1), (D2), (D3), and (D4) can react with additional phosgene to form the corresponding chloroformate dimers in a manner analogous to that shown in reaction schemes (1) and (2), and that those chloroformate dimers can react with an additional monomer of either Formula (A1a) or Formula (B1a) to form trimers in a manner analogous to that shown in reaction schemes (3), (4), (5) and (6). Eventually, provided that the stoichiometry is properly controlled in the manner discussed above, the step copolymerization can proceed in a manner generally known to those skilled in the art to form a high molecular weight copolymer.

Those skilled in the art will appreciate that if the rate constants $k_1$ and $k_2$ are approximately equal to one another, and if the rate constants $k_3$, $k_4$, $k_5$ and $k_6$ are also approximately equal to one another, then the incorporation of units corresponding to monomers (A1a) and (B1a) will be approximately random in a manner that reflects the respective monomer concentrations in the polymerization mixture. Assuming such rate equivalence of rate constants, the resulting block copolymer would tend to exhibit phase separation on a scale approaching the size of the (A1a) and (B1a) units in the copolymer, with very small domains that could be difficult to characterize by SEM, or even no phase separation at all. However, as noted above, the multi-block copolymer formed by the process of Example 21 of U.S. Pat. No. 9,416,090 has been found to exhibit a surprising degree of blockiness, as evidenced by the relatively large domains illustrated in FIG. 1.

Therefore, one explanation for the morphology shown in FIG. 1 is that the rate constants $k_1$ and $k_2$ are not approximately equal to one another, and/or the rate constants $k_3$, $k_4$, $k_5$ and $k_6$, are not approximately equal to one another. For example, if $k_1$ was significantly larger than $k_2$, the concentration of (B1a)-COCl would be lower and the rates of reactions (5) and (6) would be lower, leading to relatively slower formation of carbonate dimer (D4), relatively faster formation of carbonate dimer (D1), and greater blockiness in the resulting copolymer Likewise, if $k_3$ was significantly larger than $k_4$, $k_5$ and $k_6$, carbonate dimer (D1) would be formed relatively faster.

As noted above, in view of the need to incorporate relative amounts of the two diols that results in desired physical and mechanical properties in combination with the need for careful control of stoichiometry, it had been believed that the ability to influence the polymerization kinetics by adjustment of monomer concentration was limited. However, as illustrated in FIG. 2, and especially in FIG. 3, polymerization conditions have now been developed that favor a more random (and thus less blocky) incorporation of the comonomers. For example, the process of Example 21 of U.S. Pat. No. 9,416,090 was conducted by adding triphosgene to a mixture of PrD-di I₂DAT and EGPLLAD7k relatively slowly, over the course of 2-3 hours, resulting in a relatively blocky copolymer structure and a copolymer composition having relatively large phase domains (FIG. 1). During the synthesis of the copolymer of Example 21 of U.S. Pat. No. 9,416,090, the monomers were not rigorously dried before polymerization and the temperature of the reaction was not controlled. It has now been found that the same amounts of the same monomers can be employed to produce a copolymer composition having relatively smaller phase domains (FIG. 2) by adding the triphosgene to the mixture of PrD-di I₂DAT and EGPLLAD7k relatively quickly, and/or at an elevated temperature, or even to produce a copolymer composition not exhibiting visibly phase-separated domains by SEM (FIG. 3) by even quicker addition of triphosgene to the same well-dried monomers. This invention is not limited by theory of operation, but it is believed that, by increasing the relative phosgene concentration, such polymerization conditions enhance the relative rate at which aliphatic diol monomer (e.g., EGPLLAD) is incorporated into the copolymer as compared to the rate at which the aromatic diol monomer (e.g., PrD-di I₂DAT) is incorporated. For example, in terms of the kinetic schemes illustrated in FIGS. 4A to 4C, it is believed that the effect of such polymerization conditions is to increase the relative rate of reaction (2) to a greater extent than reaction (1), thereby enhancing the relative rates of reactions (5) and (6) relative to (3) and (4), particularly during early stages of the step copolymerization.

Various embodiments provide copolymer composition that comprise a multi-block copolymer. For example, an embodiment provides a copolymer composition comprising a multi-block copolymer comprising a first block and a second block. In an embodiment, the first block is substituted with an amount of heavy atoms that is effective to render it more radiopaque than the second block. In an embodiment, the multi-block copolymer has a number average molecular weight of 100 kDa or greater.

In some embodiments, the multi-block copolymer is in the form of a single phase. An example of such a single phase copolymer composition is illustrated in FIG. 3 (as discussed in further detail elsewhere herein). The composition of the multi-block copolymer can be selected so that the single phase has a desired glass transition temperature. For example, in an embodiment the single phase of the multi-block copolymer has a glass transition temperature that is greater than 37° C.

In other embodiments, the copolymer composition comprises two or more phases. For example, in an embodiment, the copolymer composition comprises a discontinuous first polymer phase and a continuous second polymer phase. The composition of the multi-block copolymer can be selected so that each phase has a desired glass transition temperature, which can be similar or different from one another. For example, in an embodiment, a discontinuous first polymer phase has a first glass transition temperature greater than 37° C. In an embodiment, a continuous second polymer phase has a second glass transition temperature greater than 37° C. In embodiments of phase-separated multi-block copolymers, the discontinuous first polymer phase may be relatively enriched in the first blocks of the multi-block copolymer and the continuous second polymer phase may be relatively enriched in the second blocks of the multi-block copolymer.

Copolymer compositions comprising two or more phases can have various phase morphologies. For example, in an embodiment, the copolymer composition comprises a discontinuous first polymer phase and a continuous second polymer phase. The discontinuous first polymer phase can be in the form of domains dispersed throughout the continuous second polymer phase. Examples of such a phase separated copolymer composition are illustrated in FIGS. 1 and 2 (as discussed in further detail elsewhere herein). The sizes of the dispersed domains can vary over a broad range. In some embodiments, the discontinuous first polymer phase has an average domain size that is less than 15 μm, 10 μm or less, 5 μm or less, or 1 μm or less. In an embodiment, the copolymer composition is not a multi-block copolymer that (a) comprises about 50% by weight of units of PrD-di I₂DAT and about 50% by weight of units of EGPLLAD7K and that (b) has an average domain size for the discontinuous polymer phase that is 15 μm or more.

The copolymer compositions described herein can contain a variety of multi-block copolymers. In various embodiments, the first block is substituted with an amount of heavy atoms that is effective to render it more radiopaque than the second block. For example, in various embodiments the first block of the multi-block copolymer comprises one or more units of the following Formula (A1):

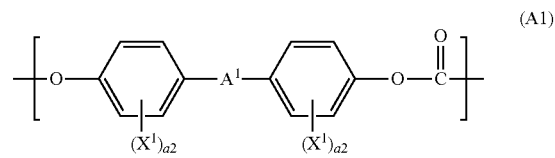

(A1)

In Formula (A1), $A^1$ is an organic spacer group containing from 4 to 30 carbon atoms; $X^1$ is I or Br; and each a2 is independently an integer in the range of zero to three, with the proviso that at least one $X^1$ is attached to at least one of the phenyl rings of the unit of the Formula (A1). The I and/or Br atoms are examples of heavy atoms that are attached to the first block in amounts that are effective to render the first block more radiopaque than the second block.

In Formula (A1), $A^1$ can be various organic spacer groups containing from 4 to 30 carbon atoms. For example, in an embodiment, the unit of the Formula (A1) is a unit represented by the following Formula (A2):

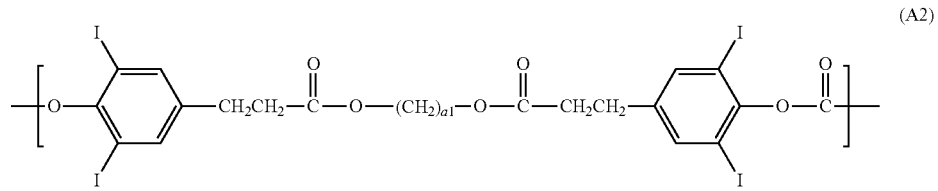

(A2)

In Formula (A2), the variable a1 is an integer in the range of 1 to 12. For example, a1 may be in the range of 2 to 6. In various embodiments, the unit of the Formula (A2) is a PrD-di I$_2$DAT carbonate unit represented by the following formula:

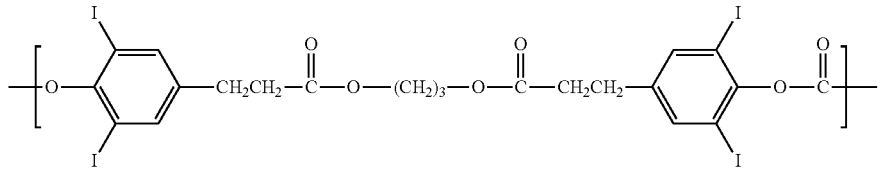

PrD-Di I$_2$DAT Carbonate Unit

Various second blocks can be incorporated into multi-block copolymers as described herein. For example, in an embodiment, the second block of a multi-block copolymer comprises one or more units of the following Formula (B1):

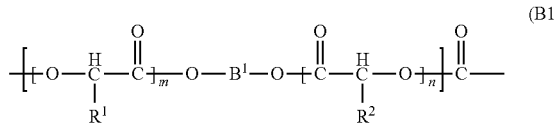

(B1)

In Formula (B1), each $R^1$ is individually H or $C_{1-6}$ alkyl. For example, in an embodiment each $R^1$ is individually hydrogen or methyl. $B^1$ is an organic spacer group containing 1-12 carbon atoms. For example, in an embodiment $B^1$ is $C_{1-12}$ alkylene. In Formula (B1), m and n are each individually integers in the range of about 10 to about 500. For example, in an embodiment, m and n are each individually integers in the range of about 30 to about 100.

In an embodiment of the copolymer composition, the unit of the Formula (B1) is a unit represented by the following Formula (B2):

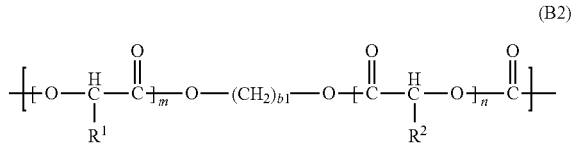

(B2)

In Formula (B2), b1 is an integer in the range of 1 to 12. In an embodiment, each $R^1$ of Formulae (B1) or (B2) is individually hydrogen or methyl and m and n are each individually integers in the range of about 30 to about 100. In an embodiment of the copolymer composition, the unit of the Formula (B2) is a unit represented by the following Formula (B3):

In Formula (B3), m1 and m2 are integers such that the sum of m1 and m2 is equal to m of Formula (B2). Similarly, the variables n1 and n2 in Formula (B3) are integers such that the sum of n1 and n2 is equal to n of Formula (B2). In an embodiment, the copolymer composition comprises a multi-block copolymer having at least one second block in which the Formula (B1) is a EGPLLAD carbonate unit of the following formula:

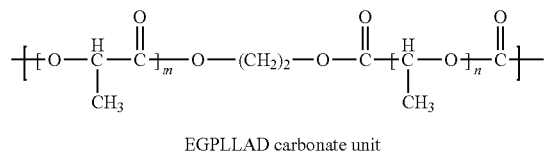

EGPLLAD carbonate unit

The copolymer compositions described herein can contain multi-block copolymers having molecular weights that vary over a broad range. In various embodiment, the multi-block copolymer has a number average molecular weight of 100 kDa or greater, about 110 kDa or greater, about 200 kDa or less, about 175 kDa or less, or any range between any of the aforementioned values. For example, in various embodiments the multi-block copolymer has a number average molecular weight in the range of about 100 kDa to about 200 kDa.

The copolymer compositions described herein can be made in various ways by those skilled in the art using routine experimentation guided by the teachings provided herein, including the working examples below and FIGS. 1-5. For example, an embodiment provides a method of making a copolymer composition as described herein, comprising copolymerizing an aromatic diol monomer of the Formula (A1a) and an aliphatic diol monomer of the Formula (B1a):

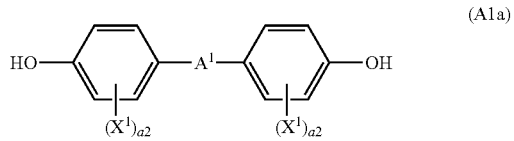

(A1a)

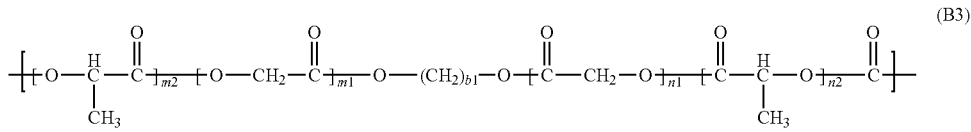

(B3)

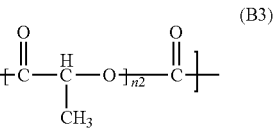

-continued

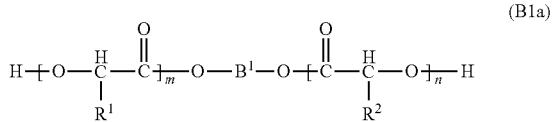

(B1a)

In Formula (A1a), $A^1$ is an organic spacer group containing from 4 to 30 carbon atoms. For example, in an embodiment $A^1$ is an organic spacer group represented by the following Formula ($A^2$):

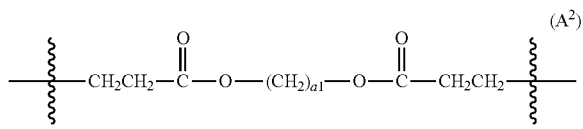

(A²)

In Formula ($A^2$), a1 is an integer in the range of 1 to 12.

In Formula (A1a), $X^1$ is I or Br. As discussed elsewhere herein, I and Br atoms are examples of heavy atoms that can be included in the aromatic diol monomer of the Formula (A1a) in amounts effective to render a first block of the resulting multi-block copolymer more radiopaque than a second block. In Formula (A1a), each a2 is independently an integer in the range of zero to three, with the proviso that at least one $X^1$ is attached to at least one of the phenyl rings of the monomer of the Formula (A1a). In various embodiments, a2 is 1 or 2. For example, in an embodiment, $X^1$ is I and a2 is 1 or 2.

In Formula (B1a), $B^1$ is an organic spacer group containing from 1 to 12 carbon atoms; each $R^1$ is individually H or $C_{1-6}$ alkyl; and m and n are each individually integers in the range of about 10 to about 500. The copolymerizing of the monomer of the Formula (A1a) and the monomer of the Formula (B1a) is conducted in the presence of a phosgene source under reaction conditions selected to form a multi-block copolymer. Those skilled in the art can select such reaction conditions by employing routine experimentation guided by the teachings provided herein.

In various embodiments, the monomer of the Formula (A1a) is a monomer represented by the following Formula (A1b):

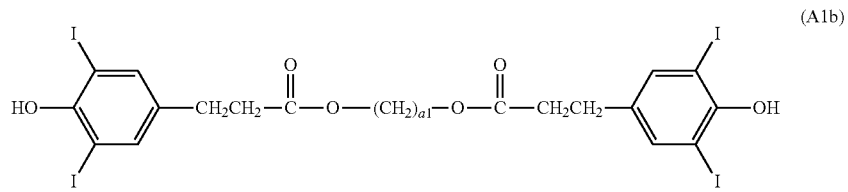

(A1b)

In Formula (A1b), a1 is an integer in the range of 1 to 12. For example, in various embodiments the monomer of the Formula (A1b) is an aromatic diol monomer of the following formula PrD-di $I_2$DAT:

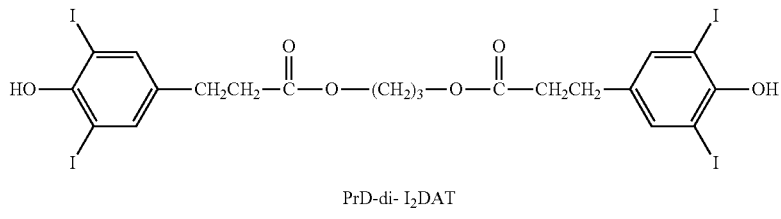

PrD-di- $I_2$DAT

In other embodiments, the monomer of the Formula (A1b) is an aromatic diol monomer of the following formula EG-di $I_2$DAT:

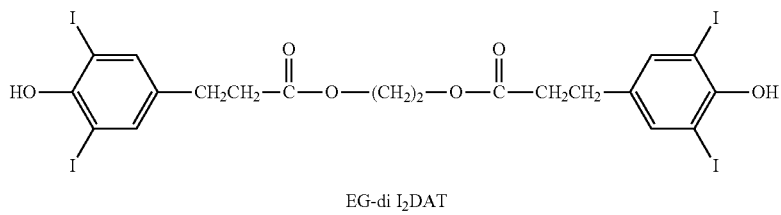

EG-di $I_2$DAT

In various embodiments, the monomer of the Formula (B1a) is a monomer represented by the following Formula (B1b):

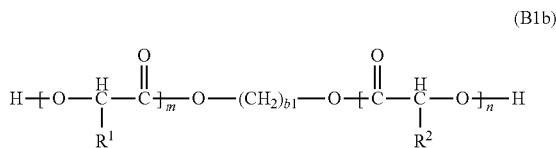
(B1b)

In Formula (B1b), b1 is an integer in the range of 1 to 12. For example, in various embodiments the monomer of the Formula (B1b) is an aliphatic diol monomer of the following formula EGPLLAD:

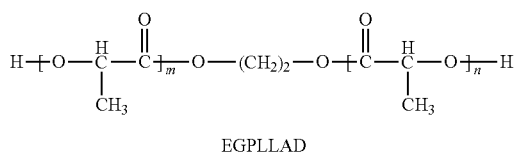

EGPLLAD

In other embodiments, the monomer of the Formula (B1b) is an aliphatic diol monomer of the following Formula EGPLGA diol:

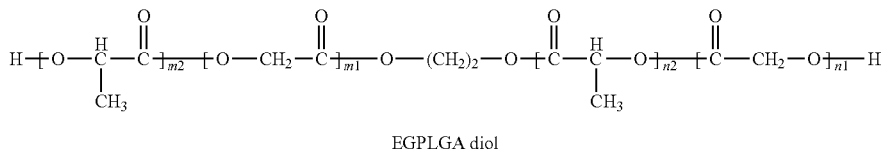

EGPLGA diol

In Formula EGPLGA diol, the variables m1 and m2 are integers such that the sum of m1 and m2 is equal to m of formula (B1b); and n1 and n2 are integers such that the sum of n1 and n2 is equal to n of formula (B1b).

The molecular weights of the aromatic diol monomers of the Formula (A1a) and the aliphatic diol monomers of the Formula (B1a) can be varied over a broad range and thus can be selected to achieve desirable properties in the resulting multi-block copolymers and/or copolymer compositions described elsewhere herein. For example, in various embodiments the number average molecular weight of the monomer of the Formula (B1a) is in the range of about 2 kDa to about 35 kDa; about 3 kDa to about 20 kDa; or about 4 kDa to about 10 kDa.

The reaction conditions for the polymerization between the aromatic diol monomers of the Formula (A1a) and the aliphatic diol monomers of the Formula (B1a) to form a multi-block copolymer can be determined by those skilled in the art using routine experimentation guided by the teachings provided herein. The relative amounts of the aromatic diol monomers of the Formula (A1a) and the aliphatic diol monomers of the Formula (B1a) can be varied over a broad range, depending on their respective molecular weights and the stoichiometry desired. For example, in various embodiments the conditions selected to form the multi-block copolymer comprise a weight ratio of the monomer of the Formula (A1a) to the monomer of the Formula (B1a) that is in the range of 7:3 to 3:7.

As discussed elsewhere herein with respect to the kinetics of polymerization illustrated in FIGS. 4A to 4C, the reaction conditions for copolymerizing the comonomers in the presence of a phosgene source to make the multi-block copolymer can be selected to favor the incorporation of one monomer with respect to another. In an embodiment the reaction conditions for making the multi-block copolymer are selected to increase the rate at which the monomer of the Formula (B1a) is incorporated into the multi-block copolymer in the presence of the phosgene source as compared to the rate at which the monomer of the Formula (A1a) is incorporated. For example, the reaction conditions that increase the rate at which the monomer of the Formula (B1a) is incorporated into the multi-block copolymer (as compared to the monomer of the Formula (A1a)) may comprise adding the phosgene source to a mixture that comprises the monomer of the Formula (A1a) and the monomer of the Formula (B1a) at a rate that is faster than the rate at which the phosgene source reacts with the monomer of the Formula (A1a). In an embodiment, the phosgene source comprises triphosgene.

In various embodiments, the copolymer compositions described herein are biocompatible, biodegradable and/or bioresorbable. In view of the manner in which their mechanical properties can be improved as taught herein, such copolymer compositions are desirable for a number of practical applications. Various embodiments of the copolymer compositions described herein may be used to produce a variety of useful articles with valuable physical and chemical properties, including incorporation into implantable medical devices. The useful articles can be shaped by conventional polymer thermo-forming techniques such as blow molding, extrusion and injection molding when the degradation temperature of the copolymer is above the glass transition and/or crystalline melt temperature, or conventional non-thermal techniques can be used, such as compression molding, injection molding, solvent casting, spin casting, and wet spinning. Combinations of two or more methods can be used. Shaped articles prepared from the copolymers are useful, inter alia, as biocompatible, biodegradable and/or bioresorbable biomaterials for medical implant applications.

Incorporation of the copolymer composition into the implantable medical device can be accomplished in various ways. For example, in some embodiments the implantable medical device is a stent that is formed by a process that includes blow molding a copolymer composition that comprises a multi-block copolymer as described herein to form a generally cylindrical shape, such as a tube, that is suitable for further processing (e.g., laser cutting) to form a stent. In other embodiments, a copolymer composition that comprises a multi-block copolymer as described herein (optionally containing a biologically active compound such as sirolimus or rapamycin) can be incorporated into and/or coated onto an implantable medical device or a portion thereof. The copolymer composition can be formulated to include a biologically active compound, e.g., a therapeutic such as a drug, thus enabling the implantable medical devices to deliver the drug at or near an in vivo site of implantation.

In various embodiment, the implantable medical device is a stent. A stent may have many different types of forms. For instance, the stent may be an expandable stent. In another embodiment, the stent may be configured to have the form of a sheet stent, a braided stent, a self-expanding stent, a woven stent, a deformable stent, or a slide-and-lock stent. Stent fabrication processes may further include two-dimensional methods of fabrication such as cutting extruded sheets of copolymer, e.g., via laser cutting, etching, mechanical cutting, or other methods, and assembling the resulting cut portions into stents, or similar methods of three-dimensional fabrication of devices from solid forms.

In other embodiments, the copolymers are formed into coatings on the surface of an implantable device, particularly a stent, made either of a copolymer as described herein or another material, such as metal. Such coatings may be formed on stents via techniques such as dipping, spray coating, combinations thereof, and the like. Further, stents may be comprised of at least one fiber material, curable material, laminated material and/or woven material. The medical device may also be a stent graft or a device used in embolotherapy.

Details of stent products and fabrication in which the polymers described herein may be employed are disclosed in U.S. Patent Publication No. 20060034769, the disclosure of which is incorporated by reference, and particularly for the purpose of describing such stent products and fabrication methods. Stents are preferably fabricated from the radiopaque copolymer compositions described herein, to permit fluoroscopic positioning of the device.

The highly beneficial combination of properties associated with preferred embodiments of the copolymer compositions described herein means that embodiments of such copolymers are well-suited for use in producing a variety of resorbable medical devices besides stents, especially implantable medical devices that are beneficially radiopaque and biocompatible, and have various times of bioresorption. For example embodiments of the copolymers are suitable for use in resorbable implantable devices with and without therapeutic agents, device components and/or coatings with and without therapeutic agents for use in other medical systems, for instance, the musculoskeletal or orthopedic system (e.g., tendons, ligaments, bone, cartilage skeletal, smooth muscles); the nervous system (e.g., spinal cord, brain, eyes, inner ear); the respiratory system (e.g., nasal cavity and sinuses, trachea, larynx, lungs); the reproductive system (e.g., male or female reproductive); the urinary system (e.g., kidneys, bladder, urethra, ureter); the digestive system (e.g., oral cavity, teeth, salivary glands, pharynx, esophagus, stomach, small intestine, colon), exocrine functions (biliary tract, gall bladder, liver, appendix, recto-anal canal); the endocrine system (e.g., pancreas/islets, pituitary, parathyroid, thyroid, adrenal and pineal body), the hematopoietic system (e.g., blood and bone marrow, lymph nodes, spleen, thymus, lymphatic vessels); and, the integumentary system (e.g., skin, hair, nails, sweat glands, sebaceous glands).

Embodiments of the copolymer compositions described herein can be used to fabricate wound closure devices, hernia repair meshes, gastric lap bands, drug delivery implants, envelopes for the implantation of cardiac devices, devices for other cardiovascular applications, non-cardiovascular stents such as biliary stents, esophageal stents, vaginal stents, lung-trachea/bronchus stents, and the like.

In addition, embodiments of the copolymer compositions described herein are suitable for use in producing implantable, radiopaque discs, plugs, and other devices used to track regions of tissue removal, for example, in the removal of cancerous tissue and organ removal, as well as, staples and clips suitable for use in wound closure, attaching tissue to bone and/or cartilage, stopping bleeding (homeostasis), tubal ligation, surgical adhesion prevention, and the like. Embodiments of the copolymer compositions described herein are also well-suited for use in producing a variety of coatings for medical devices, especially implantable medical devices. Further, in some preferred embodiments, embodiments of the inventive copolymer compositions may be advantageously used in making various resorbable orthopedic devices including, for example, radiopaque biodegradable screws (interference screws), radiopaque biodegradable suture anchors, and the like for use in applications including the correction, prevention, reconstruction, and repair of the anterior cruciate ligament (ACL), the rotator cuff/rotator cup, and other skeletal deformities.

Other devices that can be advantageously formed from embodiments of the copolymers described herein include devices designed for use in tissue engineering. Examples of suitable resorbable devices include tissue engineering scaffolds and grafts (such as vascular grafts, grafts or implants used in nerve regeneration). Embodiments of the copolymers described herein may also be used to form a variety of devices effective for use in closing internal wounds. Non-limiting examples include sutures, clips, staples, barbed or mesh sutures, implantable organ supports, and the like, for use in various surgery, cosmetic, and cardiac wound closure applications.

Various devices useful in dental applications may advantageously be formed from embodiments of the copolymer compositions described herein. For example, devices for guided tissue regeneration, alveolar ridge replacement for denture wearers, and devices for the regeneration of maxillafacial bones may benefit from having one or more of the desirable properties described herein, such as for example being radiopaque so that a surgeon or dentist can ascertain the placement and continuous function of such implants by simple X-ray imaging.

Preferred embodiments of the copolymer compositions described herein are also useful in the production of radiopaque polymeric embolotherapy products for the temporary and therapeutic restriction or blocking of blood supply to treat tumors and vascular malformations, e.g., uterine fibroids, tumors (i.e., chemoembolization), hemorrhage (e.g., during trauma with bleeding) and arteriovenous malformations, fistulas and aneurysms. Details of embolotherapy products and methods of fabrication in which embodiments of the copolymer compositions described herein may be employed are disclosed in U.S. Patent Publication No. 20050106119 A1, the disclosure of which is incorporated by reference, and particularly for the purpose of describing such products and methods. Embolotherapy treatment methods are by their very nature local rather than systemic and the products are preferably fabricated from the radio-opaque embodiments of the copolymer compositions described herein, to permit fluoroscopic monitoring of delivery and treatment.

The polymers described herein are further useful in the production of a wide variety of therapeutic agent delivery devices. Such devices may be adapted for use with a variety of therapeutics including, for example, pharmaceuticals (i.e., drugs) and/or biological agents as previously defined and including biomolecules, genetic material, and processed biologic materials, and the like. Any number of transport systems capable of delivering therapeutics to the body can be made, including devices for therapeutics delivery in the treatment of cancer, intravascular problems, dental problems, obesity, infection, and the like.

Copolymer compositions as described herein may include one or more components in addition to the multi-block copolymer, e.g., a therapeutic agent, a plasticizer, a filler, a crystallization nucleating agent, a preservative, a stabilizer, a photoactivation agent, etc., depending on the intended application. For example, in an embodiment, a medical device comprising a copolymer composition as described herein further comprises an effective amount of at least one therapeutic agent, such as a pharmaceutical agent, biological agent and/or a magnetic resonance enhancing agent. Non-limiting examples of preferred pharmaceutical agents include an immunosuppressant, a chemotherapeutic agent, a non-steroidal anti-inflammatory, a steroidal anti-inflammatory, and a wound healing agent. Therapeutic agents may be co-administered with embodiments of the copolymer composition. In a preferred embodiment, at least a portion of the therapeutic agent is contained within the copolymer composition. In another embodiment, at least a portion of the therapeutic agent is contained within a copolymer coating on the surface of a medical device.

Non-limiting examples of preferred immunosuppressants include sirolimus and everolimus. Non-limiting examples of preferred chemotherapeutic agents include taxanes, taxinines, taxols, paclitaxel, dioxorubicin, cis-platin, adriamycin, and bleomycin. Non-limiting examples of preferred non-steroidal anti-inflammatory compounds include aspirin, dexa-methasone, ibuprofen, naproxen, and Cox-2 inhibitors (e.g., Rofexcoxib, Celecoxib and Valdecoxib). Non-limiting examples of preferred steroidal anti-inflammatory compounds include dexamethasone, beclomethasone, hydrocortisone, and prednisone. Mixtures comprising one or more therapeutic agents may be used. Non-limiting examples of preferred magnetic resonance enhancing agents include gadolinium salts such as gadolinium carbonate, gadolinium oxide, gadolinium chloride, and mixtures thereof.

The amounts of additional components present in the medical device are preferably selected to be effective for the intended application. For example, a therapeutic agent is preferably present in the medical device in an amount that is effective to achieve the desired therapeutic effect in the patient to whom the medical device is administered or implanted. Such amounts may be determined by routine experimentation informed by the guidance provided herein. In certain embodiments, the desired therapeutic effect is a biological response. In an embodiment, the therapeutic agent in the medical device is selected to promote at least one biological response, preferably a biological response selected from the group consisting of thrombosis, cell attachment, cell proliferation, attraction of inflammatory cells, deposition of matrix proteins, inhibition of thrombosis, inhibition of cell attachment, inhibition of cell proliferation, inhibition of inflammatory cells, and inhibition of deposition of matrix proteins. The amount of magnetic resonance enhancing agent in a medical devices is preferably an amount that is effective to facilitate radiologic imaging, and may be determined by routine experimentation informed by the guidance provided herein.

The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" may include 1) "biomolecule", as used herein, encompassing a biologically active peptide, protein, carbohydrate, vitamin, lipid, or nucleic acid produced by and purified from naturally occurring or recombinant organisms, antibodies, tissues or cell lines or synthetic analogs of such molecules; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent may also include vitamin or mineral substances or other natural elements.

For medical devices implanted in the vascular system, e.g., a stent, the amount of the therapeutic agent is preferably sufficient to inhibit restenosis or thrombosis or to affect some other state of the stented tissue, for instance, heal a vulnerable plaque, and/or prevent rupture or stimulate endothelialization. The therapeutic agent(s) may be selected from the group consisting of antiproliferative agents, anti-inflammatory, anti-matrix metalloproteinase, and lipid lowering, cholesterol modifying, anti-thrombotic and antiplatelet agents, in accordance with preferred embodiments. In some preferred embodiments of the stent, the therapeutic agent is contained within the stent as the agent is blended with the polymer or admixed by other means known to those skilled in the art. In other preferred embodiments of the stent, the therapeutic agent is delivered from a copolymer coating on the stent surface. In another preferred variation the therapeutic agent is delivered without a copolymer coating. In other preferred embodiments of the stent, the therapeutic agent is delivered from at least one region or one surface of the stent. The therapeutic agent may be chemically bonded to embodiments of the copolymer or carrier used for delivery of the therapeutic of at least one portion of the stent and/or the therapeutic may be chemically bonded to embodiments of the copolymer that comprises at least one portion of the stent body. In one preferred embodiment, more than one therapeutic agent may be delivered.

Density of Copolymer Materials with Different Degree of Phase Separation

The degree of phase separation in example embodiments of multi-block copolymers as described herein varies with degree of phase separation. Examples of copolymers with less discrete phase separation (such as a continuous phase) have substantially higher density than examples with more phase separation (such as larger discontinuous domains). Thus the degree of phase separation influences the overall density of copolymer material.

Figure 5:
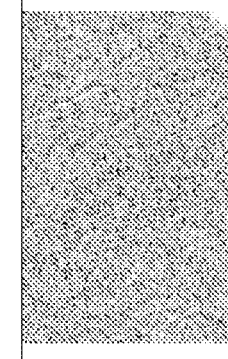
FIG. 5 shows Table 1, illustrating densities of examples of embodiments of multi-block copolymers and corresponding SEM photomicrographs.
Figure 5:
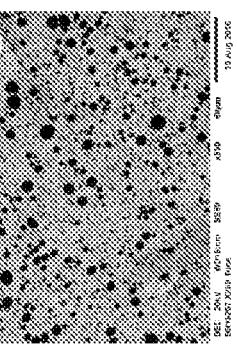
Figure 5:
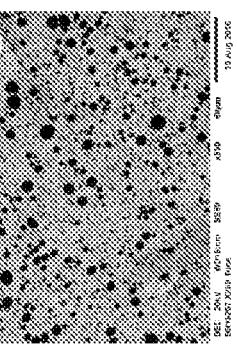

The effect of phase separation on density is illustrated in Table 1 of FIG. 5, which shows examples of the absolute (skeletal) density of blow-molded or "blown" tubes formed from three multi-block copolymers having the same overall composition (Poly(50% PrD-di I$_2$DAT-co-50% EGPLLAD7k) carbonate) but with different degrees of phase separation. These density values are provided in Table 1 along with corresponding SEM images of the copolymers. Skeletal density was measured by Micromeritics gas pycnometer method.

Mechanical Properties of Materials with Different Degrees of Phase Separation

The degree of phase separation in multi-block copolymers as described herein can have a substantial effect on material mechanical properties.

Testing of Copolymer Film Samples. Tensile properties of films prepared from Poly(50% PrD-di I$_2$DAT-co-50% EGPLLAD7k) carbonate multi-block copolymers having different degrees of phase separation were measured and are presented in Table 2. Testing was performed using rectangular strips at physiologically relevant conditions (in water at 37° C.) with the speed of deformation being 10 in/min using an Instron Tensile Tester. Films of similar thickness were prepared by compression molding at 190° C. of the corresponding copolymer powders.

The data in Table 2 demonstrate that (a) load-bearing parameters such as stress at yield and modulus tend to increase; and (b) elongation at break very substantially increases, with a decreasing size of the discontinuous phase of the multi-block copolymers. This indicates that the toughness of the multi-block copolymer material is increasing with the decrease of the size of discrete phase.

TABLE 2

Tensile properties of films prepared from multi-block copolymer Poly(50% PrD-di I2DAT-co-50% EGPLLAD7k) carbonate with different degrees of phase separation

| Test conditions | Average size of discontinuous domain | Stress at yield, ksi | Modulus, ksi | Elongation at break, % |
| --- | --- | --- | --- | --- |
| Water, 37° C. | Single phase | 8.33 ± 0.27 | 314 ± 11 | 122 ± 95 |
|  | 1 µm ≤ Size ≤ 5 µm | 7.80 ± 0.31 | 304 ± 10 | 47 ± 40 |
|  | 5 µm ≤ Size ≤ 10 µm | 7.70 ± 0.25 | 280 ± 15 | 20 ± 10 |

Testing of Blow-molded, Extruded Copolymer Tube Samples. The tensile properties of extruded/blow-molded tubes of Poly(50%PrD-di I$_2$DAT-co-50%EGPLLAD7k) carbonate multi-block copolymers with different degrees of phase separation were also measured and are presented in Table 3. Rectangular copolymer strips were cut from 3.5 mm ID blown tubes and tested in the air at room temperature (22° C.) and at physiologically relevant conditions (in water at 37° C.) with speed of deformation of 10 in/min using an Instron Tensile Tester. The data in Table 3 shows that load-bearing properties such as strength and modulus increase with a decrease of the size of discontinuous phase. Elongation at break also tends to increase with the decrease of the size of discontinuous phase, which in combination with the increase in load-bearing properties indicates substantial increase of material toughness. The difference in elongation at break between multi-block copolymers with different phase separation is especially substantial during testing in non-plasticizing conditions (e.g., in the air at a temperature of 22° C.).

TABLE 3

Tensile properties of blown tubes prepared from multi-block copolymer Poly(50% PrD-di I2DAT-co-50% EGPLLAD7k) carbonate with different degrees of phase separation

| Test conditions | Average size of discontinuous domain | Stress at yield, ksi | Modulus, ksi | Elongation at break, % |
|---|---|---|---|---|
| Water, 37° C. | Single phase | 12.2 | 319 | 203 |
| | 1 μm ≤ Size ≤ 5 μm | 11.3 | 318 | 202 |
| | 5 μm ≤ Size ≤ 10 μm | 10.0 | 292 | 199 |
| Air, 22° C. | Single phase | 14.1 | 390 | 156 |
| | 1 μm ≤ Size ≤ 5 μm | 13.6 | 338 | 153 |
| | 5 μm ≤ Size ≤ 10 μm | 11.5 | 335 | 101 |

Radiopacity of Materials with Different Degrees of Phase Separation

The degree of phase separation in multi-block copolymers as described herein with the discrete phase possessing radiopaque properties can have a substantial effect on total radiopacity of the material. Scaffolds having similar thicknesses (about 125 μm) were fabricated from Poly(50%PrD-di I$_2$DAT-co-50% EGPLLAD7k) carbonate multi-block copolymers with different degrees of phase separation and their radiopacity was measured using a FeinFocus FXS 100.24 digital x-ray system with custom software developed by CPG on a LabVIEW platform (X-ray analysis, v.1.0.1). The radiopacity was evaluated by qualitatively determining the specific difference in pixel intensity between the images of test samples and images of standard aluminum step wedges (Alloy 110, 3 mm and 0.5 mm steps) according to ASTM F640-12. The scaffolds from multi-block copolymers with discrete phase sizes less than 5μm had Equivalent Alloy Thickness Parameter values in the range of 0.70-0.81 mm, while the similar thickness scaffolds produced from the same chemical composition copolymer but with discrete phase sizes in the range of 10-15 μm had Equivalent Alloy Thickness Parameter values that were about 50% lower.

POLYMER PREPARATION EXAMPLES

Comparative Example 1

Preparation of a Multi-Block Copolymer Containing Units of PrD-Di I$_2$DAT Carbonate and Units of EGPLLAD7K Carbonate as Described in Example 21 of U.S. Pat. No. 9,416,090

In a 1 L 3-necked round-bottomed flask equipped with a mechanical stirrer, and a liquid addition device were placed 30 g (0.034 mol) of PrD-di I$_2$DAT, 30 g (0.004 mol) of EGPLLAD7K (having a number average molecular weight of about 7 kDa), 11.4 g (0.145 mol) of pyridine, and 360 mL of chloroform and stirred for 15 min to get a clear solution (the solution was slightly cloudy). Triphosgene (3.96 g, 0.04 mol of phosgene) was dissolved in 12 ml of chloroform and the solution was introduced into the reaction flask over 2-3 hours. After the addition was complete, the reaction mixture was quenched with a mixture of 135 mL of THF and 15 mL of water. 350 mL of water was added to the reaction mixture and stirred for 5 min. After allowing the layers to separate, the top aqueous layer was removed and discarded. The washing was repeated with two additional 350 mL portions of DI water. The reaction mixture was then precipitated with 700 mL of IPA. The resulting gel was ground with 550 mL of IPA twice in a 4 L blender. The product was isolated by filtration and dried in a vacuum oven at 80° C. $^1$H NMR spectrum of the polymer was in agreement with the structure. Compression molding at 190° C. of the obtained 50% EGPLLAD polymer gave a uniform transparent film.

The number average molecular weight of the obtained copolymer was about 75 kDa and it had two glass transition temperatures, at about 62° C. and at about 120° C.

Example 2

Preparation of a Multi-Block Copolymer Containing Units of PrD-Di I$_2$DAT Carbonate and Units of EGPLLAD7K Carbonate, and having Relatively Small Phase Separated Domains The reaction was carried out in a 12 L jacketed cylindrical vessel with a removable lid. The lid was equipped with a dynamic viscometer, a nitrogen inlet and outlet, pump inlet for triphosgene solution addition and a stirrer paddle. To the vessel were added 600±3 g of PrD-di I$_2$DAT and 600±3 g of EGPLLAD7K (having a number average molecular weight of about 7 kDa). The mixture was dried at 45° C. for 72 hours. After 72 hours of drying, the temperature was reduced to 22° C. and 9600±3 g of chloroform and 251±3 g of pyridine were added to the vessel. The contents were stirred until the solids went into solution. A triphosgene solution was prepared by stirring 87.7 g of triphosgene in 250.7 g of chloroform. The triphosgene solution was added to the vessel at a rate of 1.18 ml/min for 4 h. The reaction mixture was stirred for about 16 h at 22° C. and then the temperature was increased to 30° C. and stirred for 30 min. The reaction mixture was quenched by adding a mixture of 900 mL of THF and 100 mL of water.

The product was isolated from the reaction mixture in a granular powder form by precipitations with 2-propanol (IPA). The product was dried at 45° C. in vacuum oven. The product was further dried at 100° C. prior to thermal fabrication.

The number average molecular weight of the obtained copolymer was about 135 kDa and it had two glass transition temperatures, at about 62° C. and at about 120° C.

Example 3

Preparation of a Multi-Block Copolymer Containing Units of PrD-Di I$_2$DAT Carbonate and Units of EGPLLAD7K Carbonate, and having No Phase Separated Domains Visible by SEM The reaction was carried out in a 12 L jacketed cylindrical vessel with a removable lid. The lid was equipped with a nitrogen inlet and outlet, pump inlet for triphosgene solution addition and an overhead stirrer paddle. To the vessel were added 600±3 g of PrD-di I$_2$DAT and 600±3 g of EGPLLAD7K (having a number average molecular weight of about 7 kDa). The mixture was dried at 45° C. for 72h. After 72 hours of drying, the temperature was reduced to 22° C. and 9600±3 g of chloroform and 251±3 g of pyridine were added to the vessel. The contents were stirred until the solids went into solution. A triphosgene solution was prepared by stirring 87.7 g of triphosgene in 250.7 g of chloroform. Using pump the triphosgene solution was added to the vessel at a rate of 2.15 ml/min for approximately 2 h. The reaction mixture was stirred for about 1.5 h and then the temperature was increased to 30° C. and stirred for 30 min. The reaction mixture was quenched by adding a mixture of 900 mL of THF and 100 mL of water.

The product was isolated from the reaction mixture in a granular powder form by multiple precipitations with 2-propanol (IPA). The product was dried at 45° C. in vacuum oven. The product was further dried at 100° C. prior to thermal fabrication.

The number average molecular weight of the obtained copolymer was about 135 kDa and it had a glass transition temperature of about 62° C.

Example 4

Preparation of a Multi-Block Copolymer Containing Units of EG-Di I$_2$DAT Carbonate and Units of EGPLLAD7K Carbonate In a 1 L 3-necked round-bottomed flask equipped with a mechanical stirrer, and a liquid addition device were placed 50 g (0.058 mol) of EG-di I$_2$DAT, 50 g (0.0071 mol) of EGPLLAD7K (having a number average molecular weight of about 7 kDa), 11.4 g (0.276 mol) of pyridine, and 540 mL of chloroform and stirred for 15 min to get a clear solution. Triphosgene (8.73 g, 0.084 mol of phosgene) was dissolved in 31 ml of chloroform and the solution was introduced into the reaction flask over 3 hours. The reaction mixture was transferred to a 2 L beaker. With stirring 750 mL of IPA was slowly added to the reaction mixture. The polymer precipitated as a gel. The gel was transferred to a 4 L industrial blender and ground with 750 mL of IPA. The polymer was obtained as fine particles. It was dried in vacuum oven at 55° C. for 24 h and at 100° C. for 1 h. To remove the last trace of pyridine the polymer was dissolved in 600 mL of dichloromethane (DCM) in a 2 L beaker and to the resulting viscous solution 900 mL of IPA was added at a slow rate. The product precipitated as fine particles. After removal of the supernatant the precipitate was stirred with 300 mL of IPA. The last step was repeated two additional times after removing the supernatant each time. The precipitate was finally isolated by filtration and dried in vacuum oven at 55° C. for 90 h.

Example 5

Preparation of a Multi-Block Copolymer Containing Units of EG-Di I$_2$DAT Carbonate and Units of EGPLLAD15K Carbonate In a 2 L 3-necked round-bottomed flask equipped with a mechanical stirrer, and a liquid addition device were placed 50 g (0.058 mol) of EG-di I$_2$DAT, 50 g (0.0033 mol) of EGPLLAD15K (having a number average molecular weight of about 15 kDa), 22.24 mL (0.276 mol) of pyridine, and 540 mL of chloroform and stirred for 15 min to get a clear solution. Triphosgene (8.73 g, 0.084 mol of phosgene) was dissolved in 31 ml of chloroform and the solution was introduced into the reaction flask over 3 hours. The reaction mixture was transferred to a 2 L beaker. With stirring 900 mL of IPA was slowly added to the reaction mixture. The polymer precipitated as fine powder which was isolated by filtration. The precipitate was transferred back to the flask and stirred with 300 mL of IPA and then isolated by filtration. The precipitate was then dissolved 500 mL of DCM when a slightly opaque solution was obtained. The polymer was precipitated by adding 750 mL of IPA. The supernatant was removed and the precipitate was stirred with 400 mL of IPA and the polymer was isolated by filtration, washed on the filter with 250 mL of IPA. The polymer was dried in the vacuum oven at 55° C. for 100 h.

Example 6

Preparation of poly(lactide-co-glycolide) Diol of Molecular Weight 3000 (EGPLGA3000 Diol)

In a 1 L 3-necked round-bottomed flask were placed 100 g of L-lactide and 100 g of glycolide. The monomer mixture was stirred using a stainless steel stirrer under a nitrogen atmosphere. The flask was heated using an oil bath to a temperature of 50° C. for 2 h with flowing nitrogen. The temperature was increased to 110° C. and 4.23 g of ethylene glycol was added using a syringe. The temperature was increased to 150° C. and 0.12 g of Zr(acac)$_4$ was added and stirring was continued for 5 h and then allowed to cool to room temperature. To the solid mass 500 mL of chloroform was added and stirred for 24 h. Most of the solid dissolved and some gel particles were also present. The clear solution was separated and the product was precipitated by adding heptane to the solution. The solid product was isolated and dried in a vacuum oven at 45° C. for 3 days.

The product was further purified by stirring with 500 mL of acetone, and then separating the precipitate using a centrifuge. The solid product (EGPLGA3000 diol) was dried in a vacuum oven at 40° C.

Example 7

Preparation of Poly(50% PrD-Di I$_2$DAT-Co-50%PLGA3000 Carbonate)

In a 1 L 3-necked round-bottomed flask equipped with a mechanical stirrer, and a liquid addition device were placed 72 g of PrD-di I$_2$DAT, 72 g of EGPLGA3000 diol (prepared as described in Example 6), 34.7 g of pyridine, and 1150 mL of chloroform and stirred for 15 min to get a clear solution. Triphosgene (12.09 g, 0.122 mol of phosgene) was dissolved in 31 ml of chloroform and the solution was introduced into the reaction flask over 3.5 hours. The reaction mixture was quenched by adding 120 mL of 10% THF in water. With stirring 1.5 L of IPA was slowly added to the reaction mixture and then allowed to settle. The supernatant was siphoned out and the precipitate was further treated with (i) 800 mL of IPA, and (ii) 400 mL of IPA; after each treatment the supernatant was removed.

The precipitate was re-dissolved in 850 mL of dichloromethane (DCM) and then precipitated with IPA (1.5 L) and then treated with IPA as above. This step was repeated one more time and the product transferred to a 4 L industrial blender and ground with 750 mL of IPA. Finally, the product was dissolved in 700 mL of DCM. This was precipitated with 1500 mL IPA and the polymer was separated by centrifuging at 3000 rpm for 10 min. The top layer was removed and the polymer was washed 3 times with 200 mL each of IPA followed by centrifuging at 300 rpm for 10 min. The product was transferred to a glass pan and dried in a vacuum oven at 55° C. for 24 h to obtain Poly(50% PrD-diI$_2$DAT-co-50% PLGA3000 carbonate), a multi-block copolymer containing 50% units of PrD-di I$_2$DATcarbonate and 50% units of EGPLGA3000 carbonate.

Example 8

Preparation of a Multi-Block Copolymer Containing Units of PrD-Di I$_2$DAT Carbonate and Units of EGPLLAD14K Carbonate In a 3 L 3-necked jacketed flask equipped with a mechanical stirrer and a liquid addition device were placed 75 g of PrD-di I$_2$DAT, 75 g of EGPLLAD14K, 29.68 g of pyridine, and 1200 mL of chloroform and stirred for 15 min to get a clear solution. Triphosgene (10.39 g, 0.122 mol of phosgene) was dissolved in 41 ml of chloroform and the solution was introduced into the reaction flask over 2 hours. The reaction mixture was stirred overnight and then quenched by adding 120 mL of 10% THF in water. With stirring 800 mL of IPA was slowly added to the reaction mixture and then allowed to settle. The supernatant was siphoned out and the precipitate was further treated with (i) 800 mL of IPA, and (ii) 400 mL of IPA; after each treatment the supernatant was removed. The precipitate was subjected to multiple re-dissolving in DCM and re-precipitation to remove impurities. The product was transferred to a drying pan and dried in vacuum oven at 100° C. for 24 h to obtain a multi-block copolymer containing units of PrD-di I$_2$DATcarbonate and units of EGPLLAD14K carbonate.

Example 9

Preparation of a Multi-Block Copolymer Containing Units of tetraethylene glycol-Di I$_2$DAT (TEG-diI$_2$DAT) Carbonate and Units of EGPLLAD7K Carbonate In a 3 L 3-necked jacketed flask equipped with a mechanical stirrer and a liquid addition device were placed 100 g of monomer TEG-di I$_2$DAT, 100 g of PLLAD7K, 39.91 mL of pyridine, and 1081 mL of chloroform and stirred for 15 min to get a clear solution. Triphosgene (13.07 g) was dissolved in 35 ml of chloroform and the solution was introduced into the reaction flask until a viscous solution was obtained. The reaction mixture was stirred overnight and then quenched by adding 190 mL of 10% THF in water. With stirring 1500 mL of IPA was added to the reaction mixture and then allowed to settle overnight. The supernatant was siphoned out and the precipitate was further treated with 750 mL of IPA and 350 mL of IPA, after each treatment the supernatant was removed. The precipitate was isolated using a Buchner funnel under vacuum. The product was dried in a vacuum oven at 45° C. for 48 h to obtain a multi-block copolymer containing units of TEG-diI$_2$DAT carbonate and units of EGPLLAD7K carbonate.

What is claimed is:

1. A copolymer composition, comprising:
   a multi-block copolymer comprising a first block and a second block, wherein the first block is substituted with an amount of heavy atoms that is effective to render it more radiopaque than the second block and wherein the multi-block copolymer has a number average molecular weight of 100 kDa or greater;
   wherein the first block of the multi-block copolymer comprises one or more units of the following Formula (A1):

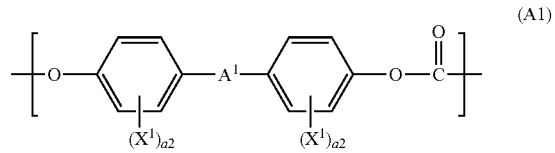

wherein
A$^1$ is an organic spacer group containing from 4 to 30 carbon atoms;
X$^1$ is I or Br;
each a2 is independently an integer in the range of zero to three, with the proviso that at least one X$^1$ is attached to at least one of the phenyl rings of the unit of the Formula (A1);
wherein the second block of the multi-block copolymer comprises one or more units of the following Formula (B1):

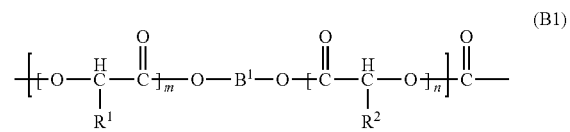

wherein
each $R^1$ is individually H or $C_{1-6}$ alkyl;
$B^1$ is an organic spacer group containing 1-12 carbon atoms;
m and n are each individually integers in the range of about 10 to about 500;
wherein the multi-block copolymer is in the form of a single phase having a glass transition temperature for the single phase that is greater than 37° C.; or
wherein the copolymer composition comprises a discontinuous first polymer phase having a first glass transition temperature greater than 37° C. and a continuous second polymer phase having a second glass transition temperature greater than 37° C., the discontinuous first polymer phase being relatively enriched in the first blocks of the multi-block copolymer and the continuous second polymer phase being relatively enriched in the second blocks of the multi-block copolymer, and wherein the first polymer phase has an average domain size of 10 μm or less; and
wherein the weight ratio of the units of the Formula (A1) to the units of the Formula (B1) is in the range of 7:3 to 3:7.

2. The copolymer composition of claim 1, wherein the multi-block copolymer is in the form of the single phase.

3. The copolymer composition of claim 1, wherein the copolymer composition comprises the discontinuous first polymer phase and the continuous second polymer phase.

4. The copolymer composition of claim 3, wherein the first polymer phase has an average domain size of less than 5 μm.

5. The copolymer composition of claim 4, wherein the first polymer phase has an average domain size of less than 1 μm.

6. The copolymer composition of claim 1, wherein the unit of the Formula (A1) is a unit represented by the following Formula (A2):

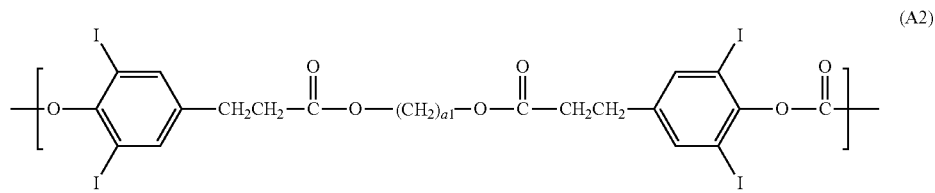

wherein a1 is an integer in the range of 1 to 12.

7. The copolymer composition of claim 6, wherein a1 is in the range of 2 to 6.

8. The copolymer composition of claim 6, wherein the unit of the Formula (A2) is a 1,3-propanediol 3,5-diiodesaminotyrosine ethyl ester (PrD-di I₂DAT) carbonate unit represented by the following formula:

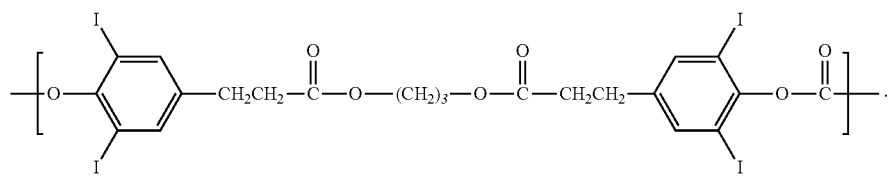

PrD-di I₂DAT carbonate unit

9. The copolymer composition of claim 1, wherein the unit of the Formula (B1) is a unit represented by the following Formula (B2):

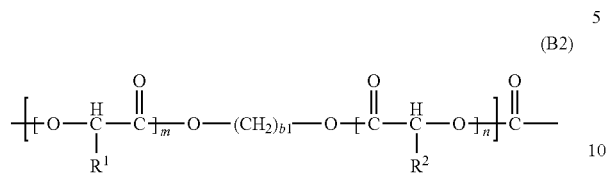
(B2)

wherein b1 is an integer in the range of 1 to 12.

10. The copolymer composition of claim 9, wherein each $R^1$ is individually hydrogen or methyl and wherein m and n are each individually integers in the range of about 30 to about 100.

11. The copolymer composition of claim 10, wherein the unit of the Formula (B2) is a unit represented by the following Formula (B3):

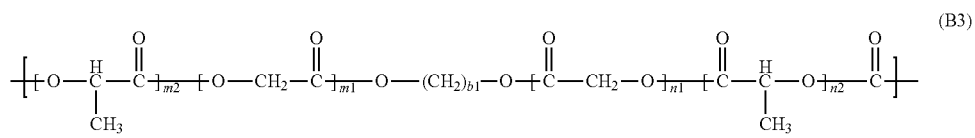
(B3)

wherein:
m1 and m2 are integers such that the sum of m1 and m2 is m; and
n1 and n2 are integers such that the sum of n1 and n2 is n.

12. The copolymer composition of claim 1, wherein the unit of Formula (B1) is an ethylene glycol poly (L-lactic acid) diol (EGPLLAD) carbonate unit of the following formula:

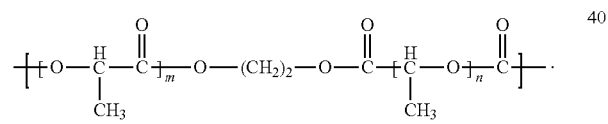

EGPLLAD carbonate unit

13. The copolymer composition of claim 2, wherein the unit of the Formula (A1) is a unit represented by the following Formula (A2):

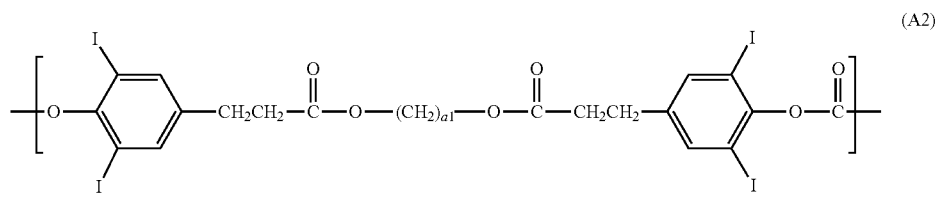
(A2)

wherein a1 is an integer in the range of 1 to 12.

14. The copolymer composition of claim 13, wherein the unit of the Formula (A2) is a 1,3-propanediol 3,5-diiodode-saminotyrosine ethyl ester (PrD-di I₂DAT) carbonate unit represented by the following formula:

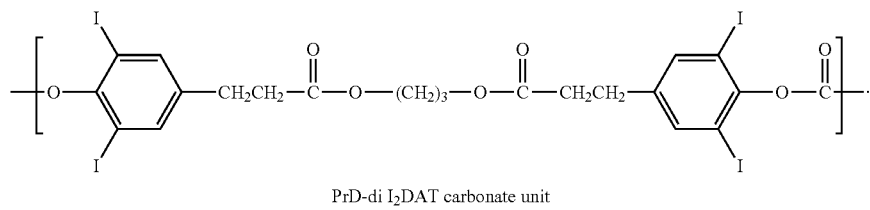

PrD-di I₂DAT carbonate unit

15. The copolymer composition of claim 14, wherein the unit of Formula (B1) is an ethylene glycol poly (L-lactic acid) diol (EGPLLAD) carbonate unit of the following formula:

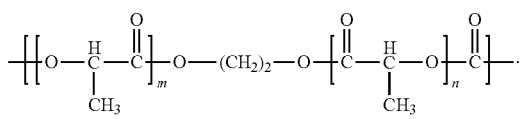

EGPLLAD carbonate unit

16. A method of making the copolymer composition of claim 1, comprising copolymerizing an aromatic diol monomer of the Formula (A1a) and an aliphatic diol monomer of the Formula (B1a):

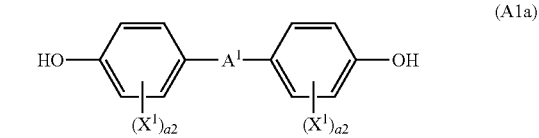 (A1a)

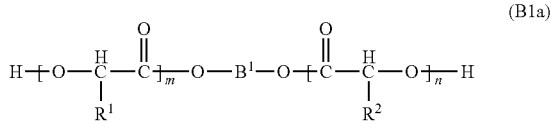 (B1a)

wherein:
$A^1$ is an organic spacer group containing from 4 to 30 carbon atoms;
$B^1$ is an organic spacer group containing from 1 to 12 carbon atoms;
each $R^1$ is individually H or $C_{1-6}$ alkyl;
X1 is I or Br;
each a2 is independently an integer in the range of zero to three, with the proviso that at least one $X^1$ is attached to at least one of the phenyl rings of the monomer of the Formula (A1a);
m and n are each individually integers in the range of about 10 to about 500; and
the copolymerizing of the monomer of the Formula (A1a) and the monomer of the Formula (B1a) is conducted in the presence of a phosgene source under reaction conditions selected to form the multi-block copolymer.

17. The method of claim 16, wherein the reaction conditions selected to form the multi-block copolymer comprise reaction conditions that increase the rate at which the monomer of the Formula (B1a) is incorporated into the multi-block copolymer as compared to the rate at which the monomer of the Formula (A1a) is incorporated.

18. The method of claim 17, wherein the reaction conditions that increase the rate at which the monomer of the Formula (B1a) is incorporated into the multi-block copolymer comprise adding the phosgene source to a mixture that comprises the monomer of the Formula (A1a) and the monomer of the Formula (B1a) at a rate that is faster than the rate at which the phosgene source reacts with the monomer of the Formula (A1a).

19. The method of claim 16, wherein the monomer of the Formula (A1a) is an aromatic diol monomer of the following formula PrD-di I₂DAT:

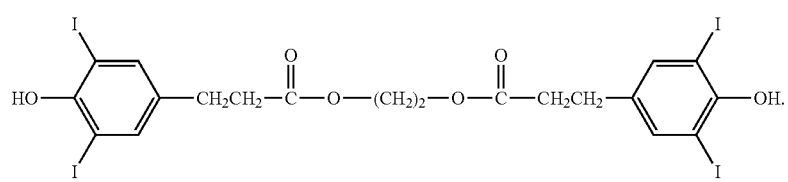

EG-di I₂DAT

20. The method of claim 19, wherein the monomer of the Formula (B1a) is an aliphatic diol monomer of the following formula EGPLLAD:

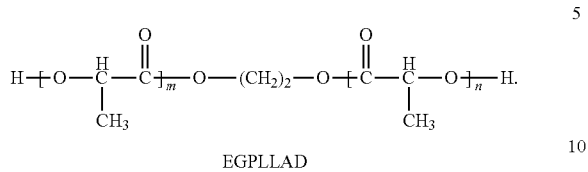

EGPLLAD

21. An implantable medical device that comprises the copolymer composition of claim 1.

22. The implantable medical device of claim 21 further comprising a biologically active compound.

23. The implantable medical device of claim 22, wherein the biologically active compound is sirolimus or rapamycin.

24. The implantable medical device of claim 21 in the form of a stent.

25. The stent of claim 24, wherein the unit of the Formula (A1) is a 1,3- propanediol 3,5-diiododesaminotyrosine ethyl ester (PrD-di $I_2$DAT) carbonate unit represented by the following formula:

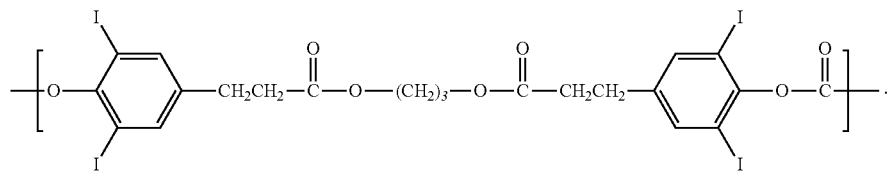

PrD-di $I_2$DAT carbonate unit

26. The stent of claim 25, wherein the unit of Formula (B1) is a EGPLLAD carbonate unit of the following formula:

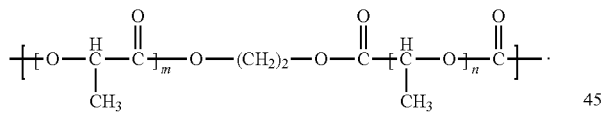

EGPLLAD carbonate unit

* * * * *